(12) United States Patent
Miao et al.

(10) Patent No.: US 11,396,559 B2
(45) Date of Patent: Jul. 26, 2022

(54) AMYLOPECTIN-BASED CYCLIC GLUCAN AND METHOD FOR PROCESSING THE SAME

(71) Applicant: Jiangnan University, Wuxi (CN)

(72) Inventors: Ming Miao, Wuxi (CN); Bo Jiang, Wuxi (CN); Chen Chen, Wuxi (CN); Yao Liu, Wuxi (CN); Yuqi Yang, Wuxi (CN); Tao Zhang, Wuxi (CN)

(73) Assignee: Jiangnan University, Wuxi (CN)

( * ) Notice: Subject to any disclaimer, the term of this patent is extended or adjusted under 35 U.S.C. 154(b) by 4 days.

(21) Appl. No.: 16/875,048

(22) Filed: May 15, 2020

(65) Prior Publication Data
US 2020/0277408 A1     Sep. 3, 2020

(30) Foreign Application Priority Data

Jul. 31, 2019  (CN) .......................... 201910699174.4
Jul. 31, 2019  (CN) .......................... 201910699411.7

(51) Int. Cl.
*C08B 30/12*     (2006.01)
*C12P 19/14*     (2006.01)

(52) U.S. Cl.
CPC ............... *C08B 30/12* (2013.01); *C12P 19/14* (2013.01)

(58) Field of Classification Search
CPC ......... C08B 30/00; C08B 30/08; C08B 30/12; C08B 30/20; C12P 19/04; C12P 19/14; C12P 19/18; C12N 9/24
See application file for complete search history.

(56) References Cited

U.S. PATENT DOCUMENTS

| 2,587,650 A | * | 3/1952 | Rist .......................... C08B 30/00 127/71 |
| 5,827,697 A | * | 10/1998 | Takaha ................ C08B 37/0015 435/101 |
| 2016/0265013 A1 | * | 9/2016 | Jonsson Wheat ....... C12P 19/18 |

FOREIGN PATENT DOCUMENTS

| CN | 105602875 A | * | 5/2016 | |
| EP | 884384 A2 | * | 12/1998 | ............. A23L 29/06 |

(Continued)

OTHER PUBLICATIONS

Bresolin, et al., Characterisation of disproportionating enzyme from wheat endosperm, Dec. 7, 2005, Planta, vol. 224, pp. 20-31 (Year: 2005).*

(Continued)

*Primary Examiner* — Stefanie J Cohen
*Assistant Examiner* — Ritu S Shirali
(74) *Attorney, Agent, or Firm* — IPRO, PLLC (57) ABSTRACT

The present disclosure discloses an amylopectin-based cyclic glucan and the processing method for the same, and belongs to the technical field of food processing. The present disclosure uses a starch as a raw material, prepares an amylopectin-based cyclic glucan through sugar chain degradation grading and glycosidase-catalyzed trans-glycoside technology, and can be used as a steady-state carrier material for food active factors. The method of the disclosure has advantages of green environmental protection, high processing yield and low cost. The prepared product has high branching degree, special large ring structure and good water solubility, and can be used for steady-state delivery and active protection of natural functional substances, involving nutritional food, medicine, daily chemicals and other fields.

13 Claims, 2 Drawing Sheets

(56) References Cited

FOREIGN PATENT DOCUMENTS

| WO | WO-0019841 A1 * | 4/2000 | ............. C08B 30/12 |
| WO | WO-2014190294 A1 * | 11/2014 | ............... C13K 1/02 |

OTHER PUBLICATIONS

Dai, et al., Comparison of starch accumulation and enzyme activity in grains of wheat cultivars differing in kernel type, 2008, Plant Growth Regulation, vol. 57, pp. 153-162 (Year: 2008).*

Maciel Filho, et al., Drying of α-amylase by spray drying and freeze-drying—a comparative study, Jul. 2014, Brazilian Journal of Chemical Engineering, vol. 31, pp. 625-631 (Year: 2014).*

Hernandez et al., Saccharification of carbohydrates in microalgal biomass by physical, chemical and enzymatic pre-treatments as a previous step for bioethanol production, Oct. 23, 2014, Chemical Engineering Journal, vol. 262, pp. 939-945 (Year: 2014).*

Ichinose, et al., Germination of Wheat Grains at Various Temperatures in Relation to the Activities of α-Amylase and Endoprotease, 2002, Plant Production Science, vol. 5, pp. 110-116 (Year: 2002).*

Sigma-Aldrich: Starch from corn [online], [retrieved on Sep. 21, 2021], Retrieved from the Internet < URL: https://www.sigmaaldrich.com/US/en/product/sial/s9679gclid=EAlalQobChMInLOhoduG8wIVh9zlCh1rlw7BEAAYASAAEgKkH_D_BwE> (Year: 2021).*

Takata et al., Strucure of the cyclic glucan produced from amylopectin by Bacillus stearothermophilus branching enzyme, 1996, Carbohydrate Research, vol. 295, pp. 91-101 (Year: 1996).*

Renge et al., Enzyme Synthesis by Fermentation Method: A Review, 2012, Scientific Reviews & Chemical Communications, 2(4), pp. 585-590 (Year: 2012).*

Convert Units: Molecular weight of Glucose [online], [retrieved on Jan. 27, 2022], Retrieved from the internet: < URL: https://www.convertunits.com/molarmass/Glucose > (Year: 2022).*

OpenWetWare: Protein Expression and Purification [online], [last edited on Nov. 20, 2007], Retrieved from the internet: < URL: https://openwetware.org/wiki/Protein_Expression_and_Purification > (Year: 2007).*

Addgene: Creating Bacterial Glycerol Stocks for Long-term Storage of Plasmids [online], [capture from Mar. 16, 2017], Retrieved from the internet: < URL: https://web.archive.org/web/20170316182002/https://www.addgene.org/protocols/create-glycerol-stock/ > (Year: 2017).*

Machine translation of CN 105602875 A originally published May 2016 to Lin et al. (Year: 2016).*

BacDive: Thermus thermophilus [online], [retrieved on Jun. 3, 2022], Retrieved from the internet: < URL: https://bacdive.dsmz.de/strain/16718 > (Year: 2022).*

* cited by examiner

AMYLOPECTIN-BASED CYCLIC GLUCAN AND METHOD FOR PROCESSING THE SAME

TECHNICAL FIELD

The disclosure belongs to the technical field of food processing, and particularly relates to an amylopectin-based cyclic glucan and the processing method for the same.

BACKGROUND

As the second largest renewable resource after cellulose in nature, starch has characteristics of low price and easy availability, degradability and easy derivatization. As a large agricultural country, China has extremely rich starch resources, and the total annual output has exceeded 27.2 million tons, but more than 90% is used to produce primary products such as starch sugar, sugar alcohol, and fermented products. There is still a large gap between the application of starch in China and developed countries, mainly reflected in that product quality is less stable than foreign products, raw material utilization rate is low, and production technology is not perfect, especially quality of high value-added products is insufficient.

At present, countries around the world attach great importance to the research on the development and utilization of starch resources. Starch-derived products are widely used in food, papermaking, textile, fine chemical, pharmaceutical and other fields. In view of a limitation of a semi-crystalline structure of an original starch, which limits its application scope and application effect, global scientific and technological workers use various methods to modify the structure and regulate the function of a starch. For example, a physical modification method, which has simple process and easy operation, but a lower degree of starch modification, and it is often used in combination with other modification methods; a chemical modification method, a chemically modified starch by this method is currently used the most in the starch industry, but its modification cost is high and a waste generated has pollution to the environment.

On the other hand, phytochemicals are a variety of low molecular weight end products produced by plant metabolism, they can protect the body against various diseases and are known as "gifts given to humans by plants". According to chemical structure or biological effect, phytochemicals are mainly divided into carotenoids, phenolic compounds, phytosterols, protease inhibitors, terpenes, sulfides, phytic acid and so on. However, many natural active ingredients have characteristics such as high melting point, poor water solubility, easy oxidative decomposition, and difficulty in digestion and absorption by the human body, therefore, there is an urgent need in this field to design effective active ingredient delivery systems to improve the utilization of biologically active substances. At present, methods for improving the utilization of natural nutrients al use cyclodextrin, protein, lipid as the matrix carrier to build phytochemical microcapsules and emulsion products. However, although existing microcapsule products using cyclodextrin as the wall material can improve the stability of the core material, the problem of low solubility in the water phase and bioavailability has not been solved. Emulsions with protein as emulsifier are sensitive to the environment and are prone to aggregation, flocculation and precipitation at the isoelectric point or under high ionic strength, leading to instability of the emulsion system, and not suitable for some food systems. Lipid carriers, etc. are susceptible to pH or enzymes in the gastrointestinal tract environment, and undergo structural damage and dislocation release of active ingredients, thus it cannot enhance its targeted cell absorption and the process is complicated.

SUMMARY

According to the present disclosure, an amylopectin-based cyclic glucan is constructed by using a combination of multiple modification methods. The method of the disclosure has advantages of green environmental protection, high processing yield and low cost. The prepared amylopectin-based cyclic glucan product has a high branching degree, a special large cyclic structure and good water solubility, and can be used for steady-state delivery and active protection of natural functional substances, involving nutritional food, medicine, daily chemicals and other fields. And using the new amylopectin-based cyclic glucan as a carrier, a phytochemical-amylopectin-based cyclic glucan inclusion is prepared by a physical field-assisted solid dispersion technique, thereby improving nutritional quality of fat-soluble functional factors and solving problems such as low solubility of natural phytochemicals, and its application range can involve functional food, medicine, cosmetics and other fields. The object of the present disclosure is achieved by the following technical solutions: a method for processing an amylopectin-based cyclic glucan and applications thereof, using a bulk starch as a raw material, preparing an amylopectin-based cyclic glucan through sugar chain degradation grading and glycosidase-catalyzed trans-glycoside technology.

The first object of the present disclosure is to provide a method for processing amylopectin-based cyclic glucan, comprising the following steps:

(1) Dispersing a defatted starch in a solvent to obtain a starch suspension, and then adding an acid catalyst to carry out a degradation reaction of the starch; wherein a concentration of the starch suspension is 1 g/mL-5 g/mL;

(2) Dissolving a starch degradation product obtained after the degradation in step (1) in a buffer solution, and then adding a trans-glycosidase preparation; the trans-glycosidase preparation can bind to and cut the α-1,4-glucosidic bond in the starch chain and cause a sugar chain to transfer to form a new cyclic chain structure. It is derived from archaea, bacteria or plants, and a ratio of sugar chain branching activity to depolymerization activity is greater than 30;

(3) Heating to inactivate an enzyme, and then an amylopectin-based cyclic glucan is obtained via isolation.

In one embodiment of the present disclosure, sugar chain branching activity of the enzyme preparation refers to activity of reducing an absorbance of a linear starch-iodine complex at 660 nm, and is based on the ability of the trans-glycosidase preparations to cut α-1,4 glycosidic bond and transfer to another glucose residue to form a cyclic chain structure to reduce linear starch fragments, branching activity (U/mL)=[(absorbance of a linear starch-iodine complex at 660 nm-absorbance of a linear starch-iodine complex with enzyme preparation at 660 nm)/(absorbance of a linear starch-iodine complex at 660 nm)]×100/10×20. Sugar chain depolymerization activity refers to activity of reducing a molecular weight of a starch, that is, an amount of enzyme required to reduce a molecular weight of a starch to 500,000 Da when the trans-glycosidase preparation reacts with 1 g of a starch substrate for 8 hours under the optimum temperature and pH conditions for glycosidase catalysis. Specific test method: molecular weight reduction activity (U/mL)=1/[(an amount of enzyme required to reduce a molecular weight of starch to 500,000 Da/1000)×(1000 mg/sample mass)]. Wherein all the activities described herein are measured at 70° C. and pH 7.0.

In one embodiment of the present disclosure, the defatted starch comprises any one of corn starch, cassava starch, potato starch, rice starch, and wheat starch with a degreasing treatment, or any one of ordinary starch and waxy starch.

In one embodiment of the present disclosure, the degreasing treatment comprises extracting a lipid ingredient in a starch using an organic solvent such as ethanol and cyclohexane.

In one embodiment of the present disclosure, the pH of the acid catalyst in the step (1) is 2.5-4.0.

In one embodiment of the present disclosure, the acid catalyst in the step (1) comprises any one or more of phosphoric acid, boric acid, organic sulfonic acid, hydrochloride, and sulfate.

In one embodiment of the present disclosure, the starch degradation reaction in the step (1) is a reaction at 20-60° C. for 30-120 minutes.

In one embodiment of the present disclosure, the step (1) specifically comprises: suspending every 10-25 g of a defatted starch in 6-10 mL of absolute ethanol, and then adding 10-100 mL of an acid catalyst solution, reacting at 20-60° C. for 30-120 minutes.

In one embodiment of the present disclosure, a volume ratio of an added amount of the acid catalyst aqueous solution to the starch suspension is (10-100):(6-10).

In one embodiment of the present disclosure, the acid catalyst solution refers to an aqueous solution of an acid catalyst.

In one embodiment of the present disclosure, the step (1) further comprises: neutralizing a pH value, grading precipitation, washing and drying to obtain a starch degradation product after the degradation reaction is completed.

In one embodiment of the present disclosure, the trans-glycosidase preparation comprises: a microorganism-derived trans-glycosidase preparation obtained by using archaea or bacterial activation culture and fermentation to produce enzymes, or a plant-derived trans-glycosidase preparation obtained by extracting from cereal grain endosperm; a ratio of sugar chain branching activity to depolymerization activity of the trans-glycosidase preparation is greater than 30;

In one embodiment of the present disclosure, the method for activation culture of archaea or bacteria comprises the following steps: taking the bacterial solution stored in a glycerol tube and inoculating it into a sterilized seed LB medium for culture under sterile conditions; the fermentation for an enzyme production comprises the following steps: inoculating into a fermentation LB medium after activation, incubating on a constant temperature shaker until the bacterial concentration OD 600=0.6, centrifuging at 10,000 rpm for 15 minutes, discarding the supernatant to collect a bacterial cell, and an enzyme preparation is obtained by steps such as lyophilization and pulverization.

In one embodiment of the present disclosure, the microbial source comprises: *Bacillus stearothermophilus* ATCC 7953, *Calditerricolayamamurae* UTM801 CGMCC 6185, *Streptococcus thermophilus* ATCC 14485, *Thermomus thermophiles* ATCC33923, Aeropyrumpernix K1 (available from the Japan Institute of Industrial Technology).

In one embodiment of the present disclosure, the preparation of the plant-derived trans-glycosidase preparation comprises the following steps: weighing cereal grains at the filling stage, adding a buffer solution, and obtaining a crude enzyme solution by homogenizing, filtering and centrifuging, which is then separated and purified by ion exchange column and gel chromatography, and obtaining an enzyme preparation by collecting and lyophilizing the active ingredients.

In one embodiment of the present disclosure, the starch degradation product is dissolved in a buffer solution to prepare a solution with a mass concentration of 2%-30%.

In one embodiment of the present disclosure, in the step (2), the buffer of the starch degradation products is heated to 60-80° C., and then the trans-glycosidase preparation is added.

In one embodiment of the present disclosure, an amount of the trans-glycosidase preparation added in the step (2) is: 600-1000 U of the trans-glycosidase preparation per 10-25 g of the defatted starch.

In one embodiment of the present disclosure, after adding the trans-glycosidase preparation in the step (2), maintaining the temperature and reacting for 8-16 hours.

In one embodiment of the present disclosure, the method specifically comprises the following steps:

(1) Weighing 10-25 g of a defatted starch and suspending it in 6-10 mL of absolute ethanol, adding 10-100 mL of an acid catalyst solution and reacting at 20-60° C. for 30-120 minutes, neutralizing a pH value, grading precipitation, washing and drying after the reaction is completed;

(2) Dissolving a starch degradation product in 50-100 mL of a phosphate buffer solution (pH 7.0) to prepare a solution with a mass concentration of 2%-30%, placing it in a 70° C. water bath and heating for 30-60 minutes, and then adding a trans-glycosidase preparation and maintaining the temperature and reacting for 8-16 hours after.

(3) Heating to inactivate an enzyme, centrifuging, drying the obtained supernatant under vacuum to obtain the target product.

The second object of the present disclosure is to provide an amylopectin-based cyclic glucan using the above methods.

In one embodiment of the present disclosure, a size of the cyclic structure in the amylopectin-based cyclic glucan is DP 19-50, a ratio of $\alpha$-1,6 glycosidic bond is 5.0-7.0%, and a molecular weight is 3000-9000 Da.

The third object of the present disclosure is to provide a method for improving nutritional quality of a phytochemical, comprising the following steps:

(1) Using the above processing method to prepare an amylopectin-based cyclic glucan: dispersing a defatted starch in a solvent to obtain a 1 g/mL-5 g/mL starch suspension, and adding an acid catalyst to perform a starch degradation reaction; after the degradation is completed, dissolving the obtained starch in a buffer, and adding a trans-glycosidase preparation; the trans-glycosidase preparation comprises: a microorganism-derived trans-glycosidase preparation obtained by using archaea or bacterial activation culture and fermentation to produce enzymes, or a plant-derived trans-glycosidase preparation obtained by extracting from cereal grain endosperm; a ratio of sugar chain branching activity to depolymerization activity of the trans-glycosidase preparation is greater than 30;

(2) Dispersing the amylopectin-based cyclic glucan in the step (1) in water to prepare a amylopectin-based cyclic glucan solution of 0.5-10 mg/mL, and then adding a phytochemical and mixing to obtain a phytochemical-amylopectin-based cyclic glucan inclusion; wherein a mass ratio of the amylopectin-based cyclic glucan to the phytochemical is (1-10):(0.5-10).

In one embodiment of the present disclosure, sugar chain branching activity of the enzyme preparation refers to activity of reducing an absorbance of a linear starch-iodine complex at 660 nm, and is based on the ability of the trans-glycosidase preparations to cut α-1,4 glycosidic bond and transfer to another glucose residue to form a cyclic chain structure to reduce linear starch fragments, specific test method: branching activity (U/mL)=[(absorbance of a linear starch-iodine complex at 660 nm-absorbance of a linear starch-iodine complex with enzyme preparation at 660 nm)/ (absorbance of a linear starch-iodine complex at 660 nm)]× 100/10×20. Sugar chain depolymerization activity refers to activity of reducing a molecular weight of a starch, that is, an amount of enzyme required to reduce a molecular weight of a starch to 500,000 Da when the trans-glycosidase preparation reacts with 1 g of a starch substrate for 8 hours under the optimum temperature and pH conditions for glycosidase catalysis. Specific test method: molecular weight reduction activity (U/mL)=1/[(an amount of enzyme required to reduce a molecular weight of starch to 500,000 Da/1000)× (1000 mg/sample mass)]. Wherein all the activities described herein are measured at 70° C. and pH 7.0.

In one embodiment of the present disclosure, the step (2) is to disperse the amylopectin-based cyclic glucan and the phytochemical respectively in water to prepare an amylopectin-based cyclic glucan solution and a phytochemical solution, and then mix them.

In one embodiment of the present disclosure, the concentration of the phytochemical solution is 0.2-0.5 mg/mL.

In one embodiment of the present disclosure, a mass ratio of the phytochemical solution to the amylopectin-based cyclic glucan solution is 5: 1-20:1.

In one embodiment of the present disclosure, a defatted starch in the step (1) is any one of corn starch, cassava starch, potato starch, rice starch, and wheat starch with a degreasing treatment, or any one of ordinary starch and waxy starch.

In one embodiment of the present disclosure, the degreasing treatment comprises extracting a lipid ingredient in a starch using an organic solvent such as ethanol and cyclohexane.

In one embodiment of the present disclosure, the pH of the acid catalyst in the step (1) is 2.5-4.0.

In one embodiment of the present disclosure, the acid catalyst in the step (1) comprises any one or more of phosphoric acid, boric acid, organic sulfonic acid, hydrochloride, and sulfate.

In one embodiment of the present disclosure, a ratio of sugar chain branching activity to depolymerization activity of the trans-glycosidase preparation is greater than 30; The trans-glycosidase preparation may be derived from any one or more of archaea, bacteria, and plants.

In one embodiment of the present disclosure, the method for activation culture of archaea or bacteria comprises the following steps: taking the bacterial solution stored in a glycerol tube and inoculating it into a sterilized seed LB medium for culture under sterile conditions; the fermentation for an enzyme production comprises the following steps: inoculating into a fermentation LB medium after activation, incubating on a constant temperature shaker until the bacterial concentration OD 600=0.6, centrifuging at 10,000 rpm for 15 minutes, discarding the supernatant to collect a bacterial cell, and an enzyme preparation is obtained by steps such as lyophilization and pulverization.

In one embodiment of the present disclosure, the microbial source comprises: *Bacillus stearothermophilus* ATCC 7953, *Calditerricolayamamurae* UTM801 CG MCC 6185, *Streptococcus thermophilus* ATCC 14485, *Thermomus thermophiles* ATCC33923, Aeropyrumpernix K1 (available from the Japan Institute of Industrial Technology).

In one embodiment of the present disclosure, the preparation of the plant-derived trans-glycosidase preparation comprises the following steps: weighing cereal grains at the filling stage, adding a buffer solution, and obtaining a crude enzyme solution by homogenizing, filtering and centrifuging, which is then separated and purified by ion exchange column and gel chromatography, and obtaining an enzyme preparation by collecting and lyophilizing the active ingredients.

In one embodiment of the present disclosure, the method for processing an amylopectin-based cyclic glucan in the step (1) specifically comprises the following steps:

(1) weighing 10-25 g of a degreased starch and suspending it in 6-10 mL of absolute ethanol, keeping adding 10-100 mL of an acid catalyst solution and reacting at 20-60° C. for 30-120 minutes, neutralizing a pH value, grading precipitation, washing and drying after the reaction is completed;

(2) dissolving a starch degradation product in 50-100 mL of a phosphate buffer solution (pH 7.0) to prepare a solution with a mass concentration of 2%-30%, placing it in a 70° C. water bath and heating for 30-60 minutes, and then adding a trans-glycosidase preparation and maintaining the temperature and reacting for 8-16 hours.

(3) heating to inactivate an enzyme, centrifuging, drying the obtained supernatant under vacuum to obtain the target product.

In one embodiment of the present disclosure, the step (2) is mixing the phytochemical with the amylopectin-based cyclic glucan under the condition of 30-50° C.

In one embodiment of the present disclosure, the mixing is performed at a rotation speed of 1000-4000 rpm for 0.5-5 hours.

In one embodiment of the present disclosure, it can also be homogenized at 10,000 to 15000 rpm for 1-5 minutes after mixing in the step (2).

In one embodiment of the present disclosure, it can also be placed in ultrasound after homogenization, and the treatment is performed at 0-10° C. for 2-20 minutes with a power controlled at 200-500 W.

In one embodiment of the present disclosure, the step (2) further comprises: centrifuging the mixed system after mixing well, taking the supernatant and drying to obtain a phytochemical-amylopectin-based cyclic glucan inclusion.

In one embodiment of the present disclosure, the method specifically comprises the following steps:

(1) weighing 10-25 g of a defatted starch and suspending it in 6-10 mL of absolute ethanol, adding 10-100 mL of an acid catalyst solution and reacting at 20-60° C. for 30-120 minutes, neutralizing a pH value, grading precipitation, washing and drying after the reaction is completed; dissolving a starch degradation product in 50-100 mL of a phosphate buffer solution (pH 7.0) to prepare a solution with a mass concentration of 2%-30%, placing it in a 70° C. water bath and heating for 30-60 minutes, and then adding a trans-glycosidase preparation and maintaining the temperature and reacting for 8-16 hours; heating to inactivate an enzyme, centrifuging, drying the obtained supernatant under vacuum to obtain an amylopectin-based cyclic glucan.

(2) weighing a certain mass of amylopectin-based cyclic glucan and natural phytochemical, wherein the former is dissolved in purified water to prepare a concentration of 0.5-10 mg/mL, and the latter is dissolved in absolute ethanol to prepare a concentration of 0.2-0.5 mg/mL.

(3) adding the guest phytochemical solution to the main amylopectin-based cyclic glucan solution at a ratio of 5:1-20:1, placing in a water bath at 30-50° C. and stirring for 0.5-5 hours at a speed of 1000-4000 rpm, and then homogenizing at 10,000-15000 rpm for 1-5 minutes.

(4) placing it in an ultrasonic action device, and a treatment is performed at 0-10° C. for 2-20 minutes with a power controlled at 200-500 W.

(5) centrifuging, drying the obtained supernatant under vacuum to obtain a phytochemical-amylopectin-based cyclic glucan inclusion with a high nutritional quality.

In one embodiment of the present disclosure, a molecular weight of the amylopectin-based cyclic glucan is 3000-7000 Da, the cyclic structure is composed of 6.5% α-1,6 glycosidic bonds and 93.5% α-1,4 glycosidic bonds, and the average size is DP21.

In one embodiment of the present disclosure, the phytochemical comprises natural products such as curcumin, quercetin, β-carotene, lutein, lycopene, capsaicin, resveratrol, and phytosterols, and one or more fat-soluble functional factors.

The fourth object of the present disclosure is to provide a phytochemical-amylopectin-based cyclic glucan inclusion.

The fifth object of the present disclosure is to apply the above-mentioned phytochemical-amylopectin-based cyclic glucan inclusion to the field of functional food, medicine, and cosmetics.

The Beneficial Technical Effects of the Present Disclosure are:

1) The starch processing method of the present disclosure has simple steps, easy operations, controllable reaction conditions, and relatively low cost. Moreover, by adopting the production process of the present disclosure, the starch raw material can be fully utilized, the atomic economy is good, substantially no byproducts are generated, and substantially pollution-free to the environment. The molecular weight of the obtained amylopectin-based cyclic glucan is 3000-9000 Da, in which a size of the cyclic structure in the amylopectin-based cyclic glucan is DP 19-50, a ratio of α-1,6 glycosidic bond is 5.0-7.0% (a ratio of α-1,6 glycosidic bonds is higher, representing a better degree of branching), with a yield of 6.0-20.0%.

2) The amylopectin-based cyclic glucan prepared by the present disclosure has a high degree of branching, a special large cyclic structure and a good water solubility, and a narrow particle size range, and belongs to a nano-scale carrier material, and can play an important role in the steady-state delivery and activity protection of fat-soluble functional substances such as functional lipids, carotenoid compounds, and flavonoid compounds.

3) The present disclosure makes full use of China's resource-rich starch to design a method for processing amylopectin-based cyclic glucan to create products with different application properties, increases added value of starch, expands application field of starch, and meets requirements for starch structure and performance in the application industry. The product prepared by the present disclosure can be applied to a variety of fields such as food, medicine, and daily chemicals, and has a very promising market prospect and vast economic benefits.

4) The present disclosure significantly improves the solubility and carrying capacity of natural phytochemicals, greatly improves the absorption and metabolism of phytochemicals in the body, thereby increasing its bioavailability, and really meets health demands of consumers for modern functional foods. A particle diameter of the obtained phytochemical-amylopectin-based cyclic glucan inclusion is 100-1000 nm, and a loading rate of phytochemicals is greater than 1.3%; a solubility in water is increased by 10-250 times, and a permeability of $CaCO_2$ cell membrane is increased by more than 3 times.

5) The method for improving nutritional quality of phytochemicals according to the present disclosure has simple steps and controllable reaction conditions, realizes continuous and low-cost green production, and makes full use of China's resource-rich natural phytochemicals to design a starch-based steady-state transportation system with targeted transport and activity protection of fat-soluble active factors, improves nutritional quality of modern foods and realizes a manufacture of personalized and nutritionally accurate foods.

6) The product prepared by the method for improving the nutritional quality of phytochemicals according to the present disclosure has functions of preventing diseases, treating diseases, and maintaining human health, and can be directly put on market as an end product for consumers, and can also be used as raw materials for food, medicine, and daily chemicals. It has high added value in science and technology, has a broad potential market, can greatly increase value of agricultural and sideline products, is of great significance to improve people's health, and has high social and economic benefits.

DETAILED DESCRIPTION

Figure 1:
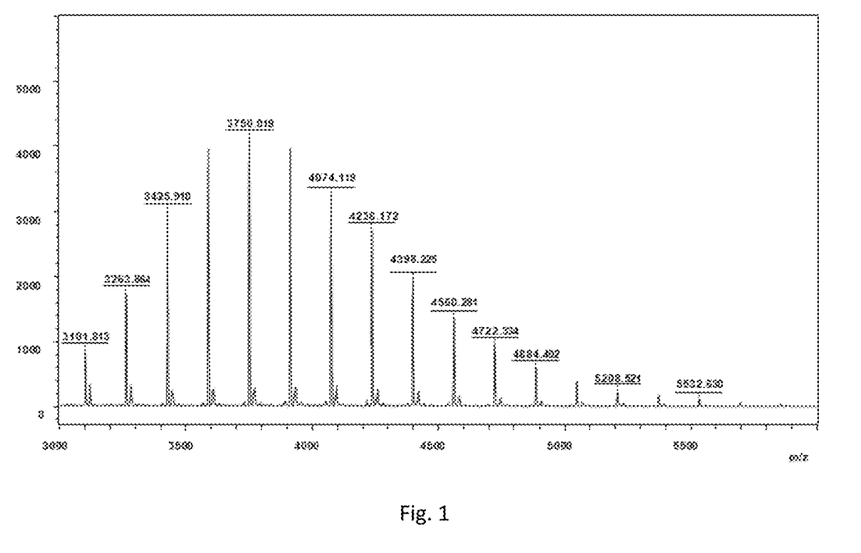
FIG. 1. MALDI-TOF-MS mass spectrum of an amylopectin-based cyclic glucan.
Figure 2:
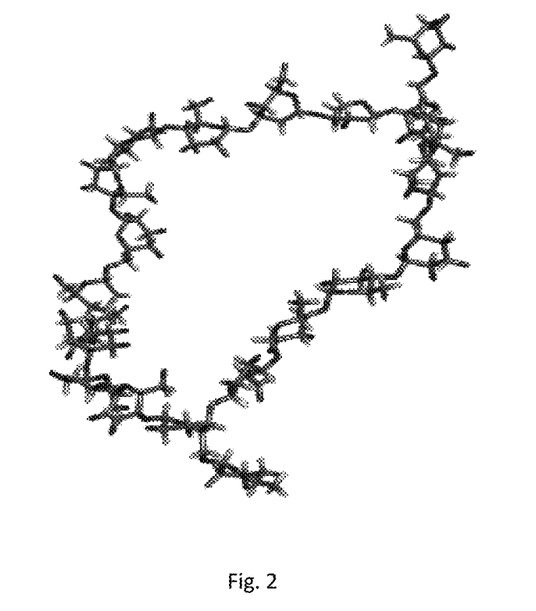
FIG. 2. Three-dimensional conformation of an amylopectin-based cyclic glucan.
Figure 3:
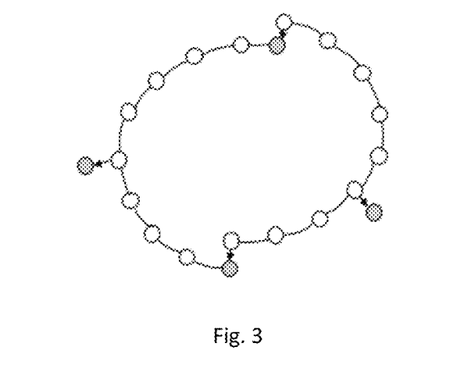
FIG. 3. Cyclic structure configuration of an amylopectin-based cyclic glucan.
Figure 4:
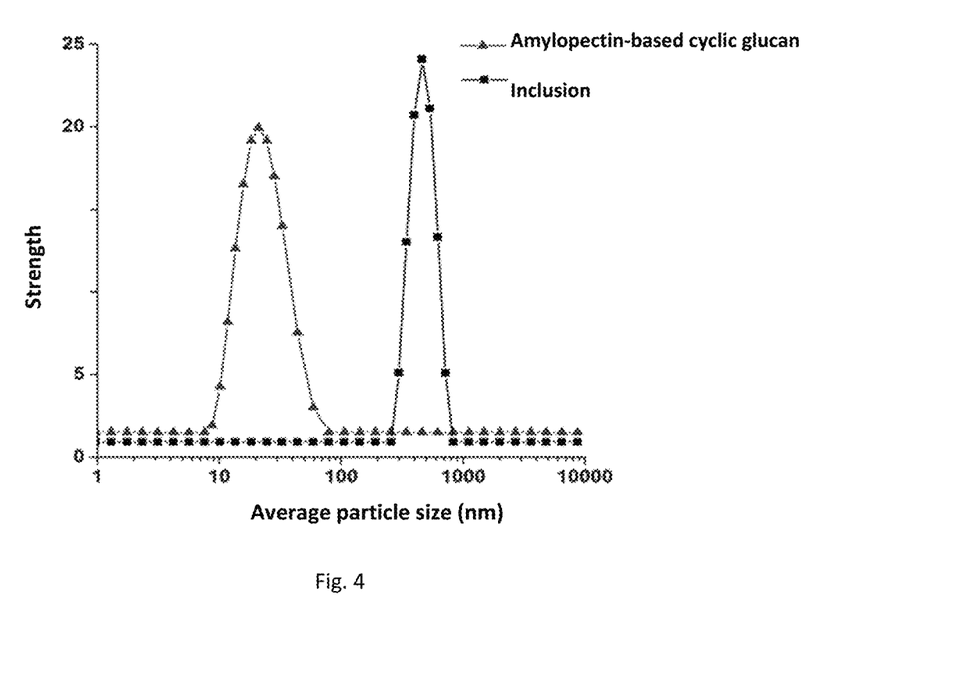
FIG. 4. The particle size distribution of β-carotene-amylopectin-based cyclic glucan in Example 1.

The content of the present disclosure will be further clarified below with reference to examples, but the content protected by the present disclosure is not only limited to the following examples.

Particle size measurement: the sample to be measured is prepared into a 0.1% (w/v) solution, and the particle size distribution is measured with a Malvern Nano ZS analyzer at 25° C.

Solubility measurement 20 mg of inclusion is weighed accurately and dissolved in 1 mL of deionized water, equilibrates at room temperature for 12 hours in the dark, and is centrifuged at 4° C. (3000 rpm, 5 minutes) to remove insoluble substances. 0.2 mL of the centrifugal solution is taken and added 4 times the volume of absolute ethanol, vortexed for 15 minutes, and centrifuged (10,000 rpm, 5 minutes) and separated to extract the phytochemical ingredients and starch. Take the supernatant and measure the absorbance with a UV spectrometer, and calculate the solubility by substituting the absorbance into the standard curve equation.

Loading ratio calculation: with reference to the soluble phytochemical content (W) and soluble starch mass (M) obtained by a solubility measurement, and a loading ratio calculation formula is as followed loading ratio (%)=W/M× 100.

$CaCO_2$ cell membrane permeability measurement: cell membrane permeability is a mass percentage of phytochemicals in $CO_2$ cells and a basal part of a lower layer of a isolation cavity to phytochemicals initially added to a upper layer of cells, and a Millicell-ERS electronic voltmeter is used to measure a transepithelial resistance value inside and outside a cell monolayer culture cavity, so as to monitor the tightness between epithelial cells and determine a integrity of a cell monolayer.

Preparation of Trans-Glycosidase Preparations

A. plant-derived trans-glycosidase preparation: it is obtained by extracting from growing cereal grain endosperms, weighing 100 g of growing cereal grains, adding 300 mL phosphate buffer solution (pH 7.2, 50 mM), and obtaining a crude enzyme solution by homogenizing, filtering and centrifuging, which is then separated and purified by ion exchange column and gel chromatography, and obtaining an enzyme preparation by collecting and lyophilizing the active ingredients. Wherein the endosperm of plant cereal grains comprises: endosperm of rice grains, endosperm of wheat grains, endosperm of corn grains, endosperm of sorghum grains and the like.

B. microorganism-derived trans-glycosidase preparation: using archaea or bacteria screened from nature via steps such as activation culture and fermentation to produce enzymes, wherein strain activation: taking a bacterial solution stored in a glycerol tube and inoculating it into a sterilized 250 mL erlenmeyer flask with 100 mL seed LB medium, incubating at 37° C. for 12 hours. Fermentation culture: inoculating with an inoculation amount of 2% (v/v) into a 250 mL erlenmeyer flask containing 100 mL fermentation LB medium under sterile conditions. After inoculation, incubating on a 37° C. constant temperature shaker until a bacterial concentration of OD600=0.6, and centrifuging at 10,000 rpm for 15 minutes, discarding the supernatant to collect a bacterial cell, and an enzyme preparation is obtained by steps such as lyophilization and pulverization. The microorganism comprises: *Bacillus stearothermophilus* ATCC 7953, *Calditerricolayamamurae* UTM801 CGMCC 6185, *Streptococcus thermophilus* ATCC 14485, *Thermomus thermophiles* ATCC33923, Aeropyrumpernix K1 (available from the Japan Institute of Industrial Technology).

Example 1

Weighing 25 g of a defatted waxy corn starch and suspending it in 10 mL of absolute ethanol, adding 100 mL of a boric acid solution (pH 2.5) and reacting at 40° C. for 120 minutes, neutralizing a pH value, grading precipitation, washing and drying after the reaction is completed;

Dissolving the obtained starch degradation product in 100 mL of a phosphate buffer solution (pH 7.0) to prepare a solution with a mass concentration of 2%, placing in a 70° C. water bath and heating for 30 minutes, and then adding 600 U of rice-derived trans-glycosidase preparation (sugar chain branching activity/depolymerization activity=52) and maintaining the temperature and reacting for 16 hours, heating and inactivating enzymes, centrifuging, and drying the obtained supernatant under vacuum to obtain the target product of an amylopectin-based cyclic glucan.

The average molecular weight of the obtained amylopectin-based cyclic glucan is 4200 Da, in which a size of the cyclic structure is DP 21, a ratio of α-1,6 glycosidic bonds is 6.0%, and a yield is 12.7%.

Example 2

Weighing 20 g of a defatted waxy rice starch and suspending it in 8 mL of absolute ethanol, adding 80 mL of a hydrochloride solution (pH 4.0) and reacting at 50° C. for 90 minutes, neutralizing a pH value, grading precipitation, washing and drying after the reaction is completed;

Dissolving the obtained starch degradation product in 70 mL of a phosphate buffer solution (pH 7.0) to prepare a solution with a mass concentration of 15%, placing in a 70° C. water bath and heating for 40 minutes, and then adding 800 U of *Bacillus stearothermophilus*-derived trans-glycosidase preparation (sugar chain branching activity/depolymerization activity=31) and maintaining the temperature and reacting for 12 hours, heating and inactivating enzymes, centrifuging, and drying the obtained supernatant under vacuum to obtain the target product.

The average molecular weight of the obtained amylopectin-based cyclic glucan is 3500 Da, in which a size of the cyclic structure is DP 20, a ratio of α-1,6 glycosidic bonds is 5.2%, and a yield is 9.7%.

Example 3

Weighing 25 g of a defatted waxy potato starch and suspending it in 6 mL of absolute ethanol, adding 60 mL of a phosphoric acid solution (pH 3.0) and reacting at 60° C. for 60 minutes, neutralizing a pH value, grading precipitation, washing and drying after the reaction is completed;

Dissolving the obtained starch degradation product in 50 mL of a phosphate buffer solution (pH 7.0) to prepare a solution with a mass concentration of 10%, placing in a 70° C. water bath and heating for 35 minutes, and then adding 700 U of *Thermomus thermophiles*-derived trans-glycosidase preparation (sugar chain branching activity/depolymerization activity=75) and maintaining the temperature and reacting for 10 hours, heating and inactivating enzymes, centrifuging, and drying the obtained supernatant under vacuum to obtain the target product. *Thermomus thermophiles*-derived is *Thermus thermophiles* CGMCC 6186.

The average molecular weight of the obtained amylopectin-based cyclic glucan is 7850 Da, in which a size of the cyclic structure is DP 35, a ratio of α-1,6 glycosidic bonds is 6.6%, and a yield is 18.1%.

Example 4 Application of the Product Obtained in Examples 1-3 as a Carrier

Dissolving the amylopectin-based cyclic glucan obtained in Examples 1-3 in purified water to prepare a solution with a concentration of 0.5 mg/mL; dissolving β-carotene in absolute ethanol to make a mass concentration of 0.2 mg/mL; adding β-carotene solution to the main amylopectin-based cyclic glucan solution at a ratio of 5:1, placing it in a water bath at 40° C. and stirring for 2 hours at a speed of 4000 rpm, and then homogenizing at 15000 rpm for 1 minutes; placing it in an ultrasonic action device, and a treatment is performed at 0° C. for 12 minutes with a power controlled at 200 W; centrifuging, drying the obtained supernatant under vacuum to obtain the corresponding β-carotene-amylopectin-based cyclic glucan inclusion.

The results of the obtained β-carotene-amylopectin-based cyclic glucan inclusions are shown in Table 1.

TABLE 1

Performance results of β-carotene-amylopectin-based cyclic glucan inclusions prepared from different amylopectin-based cyclic glucans.

|  | Average particle size (nm) | Loading ratio (%) | Solubility in water (increased multiples over uninclusion) | $CaCO_2$ cell membrane permeability (increased multiples over uninclusion) |
|---|---|---|---|---|
| Example 1 | 275 | 1.2 | 130 | 4.1 |
| Example 2 | 268 | 1.5 | 150 | 4.5 |
| Example 3 | 293 | 1.1 | 124 | 3.9 |

The uninclusion refers to pure β-carotene.

Comparative Embodiment 1

Referring to Example 1, the trans-glycosidase preparation is replaced with 4-α-glycosyltransferase, and other conditions remained unchanged to prepare a starch product.

Including the Following Process:

Weighing 25 g of a defatted waxy corn starch and suspending it in 10 mL of absolute ethanol, adding 100 mL of a boric acid solution (pH 2.5) and reacting at 40° C. for 120 minutes, neutralizing a pH value, grading precipitation, washing and drying after the reaction is completed;

Dissolving the obtained starch degradation product in 100 mL of a phosphate buffer solution (pH 7.0) to prepare a solution with a mass concentration of 2%, placing in a 70° C. water bath and heating for 30 minutes, and then adding 600 U of 4-α-glycosyltransferase (sugar chain branching activity/depolymerization activity=52) and maintaining the temperature and reacting for 16 hours, heating and inactivating enzymes, centrifuging, and drying the obtained supernatant under vacuum to obtain the target product of an amylopectin-based cyclic glucan.

The average molecular weight of the obtained amylopectin-based cyclic glucan is 37500 Da, in a ratio of α-1,6 glycosidic bonds is 4.2%, without cyclic structure.

Comparative Embodiment 2

Dissolving 20 mg of maltohexaose and 200 mg of glucose-1-1 phosphate in 100 nM citric acid buffer solution (pH7.0) containing 5 mM adenosine phosphate and 20 UD-alcohol, adding 1 mg of acidifying enzyme, and reacting at 30° C. for 2 hours. Centrifuging the reaction solution, treating the supernatant at 100° C. for 5 minutes, and centrifuging to remove a denaturing enzyme protein. Adding 50 U of glucoamylase in the supernatant, and the precipitate contained 30 mg of cyclic glucan only containing α-1,4-glucoside bonds, the obtained cyclic glucan has a cyclic structure free of α-1,6 glucoside bonds.

Example 5

Dispersing a defatted corn starch in a solvent to obtain a 1 g/mL starch suspension, and adding an acid catalyst to perform a starch degradation reaction; after the degradation is completed, dissolving the obtained starch in a buffer, and adding an archaea-derived trans-glycosidase preparation (sugar chain branching activity/depolymerization activity=41) and reacting for 10 hours to obtain an amylopectin-based cyclic glucan with an average molecular weight of 4500 Da, in which the cyclic structure is composed of 6.5% α-1,6 glycosidic bonds and 93.5% α-1,4 glycosidic bonds, and the average size is DP21.

Dissolving the obtained starch samples in water to prepare a solution with a concentration of 0.5 mg/mL; dissolving β-carotene in absolute ethanol to make a solution with a mass concentration of 0.2 mg/mL; adding the β-carotene solution to the main amylopectin-based cyclic glucan solution at a ratio of 5:1, placing it in a water bath at 40° C. and stirring for 2 hours at a speed of 4000 rpm, and then homogenizing at 15000 rpm for 1 minutes; placing it in an ultrasonic action device, and a treatment is performed at 0° C. for 12 minutes with a power controlled at 200 W; centrifuging, drying the obtained supernatant under vacuum to obtain a high nutritional quality of β-carotene-amylopectin-based cyclic glucan inclusion.

An average particle size of the obtained inclusion is 280 nm, and a loading rate of the β-carotene is 1.4%; a solubility in water is 120 times higher than that of pure β-carotene, and a permeability of $CaCO_2$ cell membrane is 4.2 times higher than that of pure β-carotene.

Example 6

Dispersing a defatted rich starch in a solvent to obtain a 5 g/mL starch suspension, and adding an acid catalyst to perform a starch degradation reaction; after the degradation is completed, dissolving the obtained starch in a buffer, and adding a plant-derived trans-glycosidase preparation (sugar chain branching activity/depolymerization activity=32.1) and reacting for 8 hours to obtain an amylopectin-based cyclic glucan with an average molecular weight of 3750 Da, in which the cyclic structure is composed of 6.5% α-1,6 glycosidic bonds and 93.5% α-1,4 glycosidic bonds, and the average size is DP 21.

Dissolving the obtained starch samples in water to prepare a solution with a concentration of 10 mg/mL; dissolving curcumin in absolute ethanol to make a solution with a mass concentration of 0.5 mg/mL; adding the curcumin solution to the main amylopectin-based cyclic glucan solution at a ratio of 10:1, placing it in a water bath at 50° C. and stirring for 3 hours at a speed of 3000 rpm, and then homogenizing at 12000 rpm for 3 minutes; placing it in an ultrasonic action device, and a treatment is performed at 10° C. for 8 minutes with a power controlled at 220 W; centrifuging, drying the obtained supernatant under vacuum to obtain a high nutritional quality of curcumin-amylopectin-based cyclic glucan inclusion.

An average particle size of the obtained inclusion is 164 nm, and a loading rate of the curcumin is 2.2%; a solubility in water is 80 times higher than that of pure curcumin, and a permeability of $CaCO_2$ cell membrane is 3.5 times higher than that of pure curcumin.

Example 7

Dispersing a defatted potato starch in a solvent to obtain a 2 g/mL starch suspension, and adding an acid catalyst to perform a starch degradation reaction; after the degradation is completed, dissolving the obtained starch in a buffer, and adding a bacteria-derived trans-glycosidase preparation (sugar chain branching activity/depolymerization activity=55.0) and reacting for 12 hours to obtain an amylopectin-based cyclic glucan with an average molecular weight of 6700 Da, in which the cyclic structure is composed of 6.5% α-1,6 glycosidic bonds and 93.5% α-1,4 glycosidic bonds, and the average size is DP 21.

Dissolving the obtained starch samples in water to prepare a solution with a concentration of 5 mg/mL; dissolving lycopene in absolute ethanol to make a solution with a mass concentration of 0.3 mg/mL; adding the lycopene solution to the main amylopectin-based cyclic glucan solution at a ratio of 20:1, placing it in a water bath at 40° C. and stirring for 5 hours at a speed of 2000 rpm, and then homogenizing at 10000 rpm for 5 minutes; placing it in an ultrasonic action device, and a treatment is performed at 4° C. for 2 minutes with a power controlled at 250 W; centrifuging, drying the obtained supernatant under vacuum to obtain a high nutritional quality of lycopene-amylopectin-based cyclic glucan inclusion.

An average particle size of the obtained inclusion is 455 nm, and a loading rate of the lycopene is 1.7%; a solubility in water is 110 times higher than that of pure lycopene, and a permeability of $CaCO_2$ cell membrane is 5.2 times higher than that of pure lycopene.

Example 8. Process Optimization

Referring to example 7, the concentration of the amylopectin-based cyclic glucan solution is changed from 5 mg/mL to 0.1 mg/mL and 15 mg/mL, and the corresponding solution dosage is adjusted to ensure that a mass ratio of the amylopectin-based cyclic glucan to lycopene is the same, other conditions remain unchanged, and corresponding products are prepared. The results of the obtained products are shown in Table 2.

TABLE 2

Results of products prepared with different amylopectin-based cyclic glucans.

| Concentrations | Average particle size (nm) | Loading ratio (%) | Solubility in water (increased multiples over uninclusion) | $CaCO_2$ cell membrane permeability (increased multiples over uninclusion) |
|---|---|---|---|---|
| 0.1 mg/mL | 406 | 1.1 | 115 | 5.2 |
| 5 mg/mL | 455 | 1.7 | 110 | 5.2 |
| 15 mg/mL | 518 | 0.5 | 109 | 4.7 |

Comparative Example 3

Referring to Example 7, the amylopectin-based cyclic glucan is replaced with a β-cyclodextrin and other conditions remained unchanged to prepare a corresponding product.

The solubility of the obtained product in water is increased by 1.1 times, and the $CaCO_2$ cell membrane permeability is increased by 0.7 times.

What is claimed is:

1. A method for processing an amylopectin-based cyclic glucan, comprising:
    dispersing a defatted starch into a solvent to obtain a 1 g/mL to 5 g/mL starch suspension, wherein the dispersing step comprises: suspending 10 to 25 g of the defatted starch in 6 to 10 mL of absolute ethanol, then adding 10 to 100 mL of an acid catalyst solution comprising an acid catalyst to catalyze degradation of the defatted starch, and reacting at 20 to 60° C. for 30 to 120 minutes, thereby obtaining a starch degradation product;
    dissolving the starch degradation product into a buffer solution,
    adding a trans-glycosidase preparation to the starch degradation product,
    wherein the trans-glycosidase preparation comprises a microorganism-derived trans-glycosidase obtained by fermentation of archaea or bacteria,
    wherein a ratio of sugar chain branching activity to depolymerization activity of the trans-glycosidase preparation is greater than 30, and
    wherein the trans-glycosidase preparation is from *Calditerricolayamamurae* UTM801, CGMCC 6185, *Streptococcus* thermophiles ATCC 14485, *Thermomus* thermophiles ATCC 33923, or *Aeropyrum* pernix K1;
    heating to inactivate the enzyme in the trans-glycosidase preparation; and
    isolating the amylopectin-based cyclic glucan,
    wherein a size of a cyclic structure in the amylopectin-based cyclic glucan is DP 19 to DP 50,
    wherein a ratio of α-1,6 glycosidic bond in the amylopectin-based cyclic glucan is 5.0% to 7.0%, and
    wherein a molecular weight of the amylopectin-based cyclic glucan is 3 kDa to 9 kDa.

2. The method according to claim 1, wherein an amount of the trans-glycosidase preparation added in the dissolving step is: 600 to 1000 U of the trans-glycosidase preparation per 10 to 25 g of the defatted starch.

3. The method according to claim 1, wherein in the dispersing step, the acid catalyst is prepared as an aqueous solution with a pH value of 2.5 to 4.0 for catalysis, and a volume ratio of the added amount of the acid catalyst aqueous solution to the defatted starch suspension is 10 to 100:6 to 10.

4. The method according to claim 1, wherein in the dissolving step, the starch degradation product is dissolved in the buffer solution to prepare a solution with a mass concentration of 2% to 30%.

5. The method according to claim 1, wherein in the dissolving step, before adding the trans-glycosidase preparation, the buffer solution in which the starch degradation product is dissolved is heated to 60 to 80° C., and then the trans-glycosidase preparation is added, maintaining the temperature and reacting for 8 to 16 hours after adding the trans-glycosidase preparation.

6. The method according to claim 1, wherein a method for activation culture of archaea or bacteria comprises the following steps:
    taking a bacterial solution stored in a glycerol tube and inoculating it into a sterilized seed LB medium for culture under sterile conditions; and
    the fermentation comprises the following steps:
    inoculating a seed solution after activation culture into a fermentation LB medium,
    incubating in a constant temperature shaker to a bacterial concentration of $OD_{600}$ of 0.6,
    centrifuging at 10,000 rpm for 15 minutes,
    discarding the supernatant to collect a bacterial cell, and obtaining the trans-glycosidase preparation by steps of lyophilization and pulverization.

7. The method of claim 1, wherein a molecular weight of the amylopectin-based cyclic glucan is 3 kDa to 7 kDa.

8. The method of claim 1, wherein the acid catalyst is any one or more of phosphoric acid, boric acid, sulfonic, acid, and sulfate.

9. The method of claim 1, wherein the buffer solution is phosphate buffer.

10. The method of claim 1, wherein the cyclic structure is composed of 6.5% α-1,6 glycosidic bonds and 93.5% α-1,4 glycosidic bonds, and the average size is DP21.

11. The method of claim 1, wherein a yield is between 6.0% and 20.0%.

12. The method of claim 1, wherein the acid catalyst is boric acid.

13. The method of claim 1, wherein the acid catalyst is phosphoric acid and the trans-glycosidase preparation is from *Thermomus* thermophiles.

\* \* \* \* \*